United States Patent [19]
Takami et al.

[11] 4,323,563
[45] Apr. 6, 1982

[54] FAT EMULSION FOR INTRAVENOUS INJECTION

[75] Inventors: Toru Takami, Yokosuka; Misako Takezawa, Yokohama; Hiroyuki Ohashi; Shigeru Takeda, both of Kawasaki, all of Japan

[73] Assignee: Ajinomoto Co., Inc., Tokyo, Japan

[21] Appl. No.: 89,498

[22] Filed: Oct. 30, 1979

[30] Foreign Application Priority Data

Oct. 31, 1978 [JP] Japan .................... 53-134279

[51] Int. Cl.$^3$ .............. A61K 31/685; C07F 9/02; C07F 9/10; C11C 3/00
[52] U.S. Cl. ................................ 424/199; 424/361; 424/195; 260/403
[58] Field of Search .................. 424/195, 199, 361; 260/403

[56] References Cited

U.S. PATENT DOCUMENTS 2,931,818  4/1960  McQuarrie ..................... 260/403
2,945,869  7/1960  Meyer et al. .................... 260/403

FOREIGN PATENT DOCUMENTS 770426  3/1957  United Kingdom .............. 424/199
770427  3/1957  United Kingdom .............. 424/199

OTHER PUBLICATIONS

Tokumura et al., Agric. Biol. Chem. 42 (3), pp. 515–521, Mar. 1978.

*Primary Examiner*—Donald B. Moyer
*Attorney, Agent, or Firm*—Oblon, Fisher, Spivak, McClelland & Maier

[57] ABSTRACT

A pharmaceutically acceptable emulsifier for preparing fat emulsions for intravenous injection comprising purified phospholipid of vegetable origin, containing less than 5% of glycolipid, and having a degree of hydrogenation of 30–50 as defined by the iodine number is prepared from vegetable phospholipid by a three-step procedure comprising (in any order) (1) isolation of a fraction containing phosphatidylcholine, (2) partial hydrogenation to produce the desired iodine value, and (3) removal of glycolipid.

20 Claims, 3 Drawing Figures

FAT EMULSION FOR INTRAVENOUS INJECTION

BACKGROUND OF THE INVENTION

1. Field of the Invention

This invention relates to a novel fat emulsion for intravenous injection.

2. Description of the Prior Art

When a fatty oil is administered to an animal by infusion, it must be administered in the form of minute particles dispersed in water by an emulsifier since fatty oils do not dissolve in water. On the other hand, because emulsifiers generally have surface activity, such an emulsion tends to produce hemolysis when administered into a blood vessel. Consequently, an emulsifier for a fat emulsion for intravenous injection should have a strong emulsifying power without bringing about hemolytic action. Thus, the quality of a fat emulsion for intravenous injection depends on the properties of the emulsifier.

The emulsification agents used hitherto have been egg yolk phospholipid or soybean phospholipid. Egg yolk phospholipid is expensive and its emulsifying capability is less than that of soybean phospholipid which, while having a better emulsifying power, is said to be less desirable due to its side effect of producing anemia. For example, when a fat emulsion using soybean phospholipid was administered to dogs, such side effects as vomiting, diarrhea and anemia occurred, and none of the dogs tested were alive at the end of four weeks. All dogs tested with egg yolk phospholipid were reported to survive (A. Wretlind, Medical Postgraduates, 7, 141, 1969).

Therefore a need has continued to exist for a fat emulsion for intravenous injection which is free of the side effects hitherto produced by such emulsions.

SUMMARY OF THE INVENTION

Accordingly, it is an object of this invention to provide a fat emulsion for intravenous injection which is free of undesirable side effects.

A further object of this invention is to provide an emulsifier for preparing such emulsions which does not produce undesirable side effects in animals to which the emulsion is administered.

A further object is to provide a process for purifying phospholipid of vegetable origin in order to make it suitable for use as an emulsifier in the emulsions of this invention.

The present inventors carried out research in order to develop a practical and excellent emulsifying agent and found that a purified phospholipid of vegetable origin in which the glycolipid content is less than 5%, said phospholipid having a hydrogenation degree of 30–50 expressed by the iodine value, is an excellent emulsifying agent not having any of the aforementioned defects. The present invention is based on this observation.

A fat emulsion for intravenous injection is a type of artificial emulsion formed by dispersion of a fatty oil in water by an emulsifier, and any side effects are due to the emulsifier used. The main side effect observed to date is anemia, which is produced after long term administration. This was observed markedly with the use of a phospholipid of vegetable origin, such as soybean phospholipid, but it has not been clear which component of the soybean phospholipid is responsible for this. The present inventors investigated soybean phospholipid and found that the cause of this side effect is the glycolipid contained in the phospholipid. By eliminating this component, they have been able to obtain a soybean phospholipid emulsifying agent which does not cause anemia.

BRIEF DESCRIPTION OF THE DRAWINGS

A more complete appreciation of the invention and many of the attendant advantages thereof will be readily attained as the same becomes better understood by reference to the following detailed description when considered with the accompanying drawings, wherein.

DETAILED DESCRIPTION OF THE PREFERRED EMBODIMENTS

Figure 1:
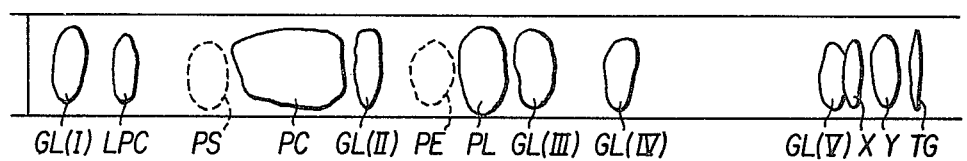
FIG. 1 is a chromatogram showing the constituents of the hydrogenated phospholipid prepared in Example 2.

In a biological test of a fat emulsion for intravenous injection, it is necessary to examine the amount of residual lipid in blood, in addition to determining the presence or absence of such side effects as anemia after long term administration. Further, fat emulsion is not a natural component in a living body, but a kind of foreign substance, and it is not possible to say that it has been utilized in vivo merely because no residual lipid is found in the blood. In other words, it is desirable that injected lipid does not accumulate and remain after being incorporated into the reticuloendothelial system of the tissues. Based on such a viewpoint, the present inventors considered that accumulation and retention of lipid in the spleen and liver, which are representative of the reticuloendothelial system tissues, should be used as criteria in evaluation of a fat emulsion, and this was carried out.

The phospholipids usable in this invention are phospholipids of vegetable origin found in soybeans, corn and rapeseed (Brassica campestris subsp. napus var. nippo-oleifera).

To produce the emulsion of this invention, the following three-step procedure can be adopted.

1. isolation of a fraction containing phosphatidylcholine.
2. partial hydrogenation (preparation of phospholipid having a specific iodine value).
3. removal of glycolipid.

Essentially the same product can be obtained by carrying out the above three steps in any order but, in consideration of yield and efficiency, it is better to carry out (1.) first, and then (2.) or (3.), and finally (3.) or (2.). It is most desirable to carry out the procedure in the order of (1.), (2.), and (3.).

Each step of purification will now be explained in detail.

Collection of the phosphatidylcholine fraction is carried out by the conventional method, using ethanol or methanol, i.e., ethanol or methanol is added to commercial soybean phospholipid (edible or powdered lecithin), the mixture is stirred at room temperature, and the insoluble fraction is removed by decantation or filtration. The remaining soluble fraction is used as the phosphatidylcholine-containing fraction. By means of this procedure, phosphatidylcholine with desirable properties as an emulsifier is concentrated from the soybean phospholipid components. The amount of ethanol or methanol used in this procedure is more than twice that of the phospholipid, and preferably more than three times. The temperature of extraction should be above room temperature, preferably 50°–60° C., and stirring and extraction for more than 20 minutes is sufficient.

The phosphatidylcholine fraction thus obtained, with or without concentration or evaporation of the solvent ethanol or methanol, can be used for the next step.

Partial hydrogenation of phospholipid is not especially difficult and a conventional method of hydrogenation can be used. In this case, the degree of hydrogenation of hydrogenated phospholipid is 30–50, preferably 35–45, as expressed by the iodine value.

For example, phospholipid is placed in an autoclave equipped with a magnetic reciprocating stirrer. Ethanol and a catalyst are added, and the mixture is contacted with hydrogen. After completion of the reaction, the catalyst is filtered off, the solvent is evaporated, and hydrogenated phospholipid is obtained as the product. The concentration of phospholipid in the solvent ethanol is below 40%, preferably 30–35%. In this case, Raney nickel can be used as a catalyst, and is added in a proportion of 3–30% (w/w) of phospholipid. Hydrogen pressure should be around 10 kg/cm$^2$ and a temperature of 40°–60° C. is desirable. However, these are correlated with reaction time, and it is not necessary to be limited to these conditions as long as a phospholipid with iodine value of 30–50 can be obtained.

Any known method can be used for the removal of glycolipid. For example, either the column method or the batch method can be used. Silicic acid or activated alumina may be used as a carrier. For example, silicic acid is introduced in a column, hydrogenated phospholipid is added, and the column is developed consecutively with chloroform, acetone and methanol. Concentration of the methanol-eluted fraction will give only the phosphatidylcholine fraction, devoid of glycolipid. In another procedure, hydrogenated phospholipid is dissolved in a mixture of chloroform and methanol (1:1, v/v), activated alumina is added, and the mixture is stirred. Activated alumina is removed by filtration and the filtrate is concentrated, by which means phospholipid not containing glycolipid can be obtained. When alumina is used, it is added in an amount three times, preferably five times, that of the phospholipid, and the mixture is stirred for about 30 minutes. In this case, a volume of solvent five times that of the phospholipid will be sufficient. As the solvent, chloroform-methanol, ethanol, methanol, ethanol-methanol, ethanol-hexane, ethanol-water, or ethanol-dichloroethylene may be used. The treatment temperature should be such that the hydrogenated phospholipid will dissolve.

Phospholipid solution after removal of glycolipid should be submitted to aseptic filtration, such as filtration through a Millipore ® filter, and then can be used as an emulsifier for the fat emulsion for intravenous injection.

The glycolipid referred to here is characterized as follows: Thin-layer chromatography of non-purified hydrogenated soybean phospholipid on a silica gel plate and development of the plate with the solvent system chloroform-methanol-water (65:25:4, v/v) will give the chromatogram shown in FIG. 1. In this chromatogram, GL(I) to GL(V) are glycolipids, among which GL(I) is not related to anemia, and GL(II), GL(III), GL(IV), and GL(V) showed side effects. Consequently, the glycolipid involved herein refers to the sum of GL(II) to GL(V).

In the production of the fat emulsion of this invention, emulsification may be carried out by conventional methods, such as ultrasonic treatment or high-pressure emulsification. In this case, the fatty oil to be used should be one of the pharmaceutically acceptable oils and fats, but there are no other limitations.

The ratio of fatty oil to water used in this invention is not especially limited, but generally the ratio is 4–20 (weight ratio) of water to 1 of fatty oil.

The amount of purified phospholipid used in this invention should be 0.05–5 parts, preferably 0.5–3 for 10 parts of fatty oil, but a more practicably desirable amount is 0.75–1.5, in order to obtain a fully satisfactory fat emulsion.

The intravenous fat emulsion manufactured by utilizing this invention has no side effects such as anemia, hitherto considered to be a side effect of fat emulsion, does not show any accumulation of lipid in the spleen, nor residual presence of lipid in blood after administration, and is a clinically desirable fat emulsion.

Having generally described this invention, a more complete understanding can be obtained by reference to certain specific examples, which are provided herein for purposes of illustration only and are not intended to be limiting unless otherwise specified.

EXAMPLE 1

A mixture of 5 kg of commercial lecithin for food (Ajinomoto product) and 10 kg of 95% ethanol was stirred at room temperature for one hour, the ethanol layer was concentrated, and the residue was used as the ethanol extract. In a 6-liter autoclave was placed 200–960 g of this ethanol extract, 1–3 liters of ethanol was added, and using a catalyst (5% Raney nickel), this was contacted with hydrogen for 40–105 minutes to effect hydrogenation. The solvent was evaporated, hexane was added to the residue in a ratio of 300 ml to 150 g of the residue, and the solution was filtered twice through a Millipore ® filter. The filtered hexane solution was added dropwise with stirring into 10 volumes of cold acetone. The precipitate formed was collected by filtration as purified hydrogenated soybean phospholipid. In accordance with the time of catalytic hydrogenation, five types of hydrogenated phospholipid with respective iodine values of 19.7, 25.4, 36.3, 49 and 71 were obtained.

EXAMPLE 2

A mixture of 1 kg of commercial powdered lecithin (Central Soya product) and 3 kg of 95% ethanol was stirred at 40°–50° C. for 30 minutes and then allowed to stand at 35° C. for 2 hours. The ethanol layer was collected and concentrated to obtain ethanol-extracted phospholipid.

This phospholipid was hydrogenated as in Example 1, and hydrogenated phospholipid (sample 1) with an iodine value of 48.4 was obtained.

Chromatography of 38 g of hydrogenated phospholipid thus obtained was carried out with 510 g of silicic acid (Mallinckrodt product) packed into a glass column (5.6×46 cm), and the column was developed consecutively with 2.4 liters of chloroform, 2.4 liters of acetone, and 9.2 liters of methanol. Methanolic fractions eluting at 1.3–6.8 liters were collected, the solvent was evaporated under reduced pressure, and the residue was dissolved in hexane. This hexane solution was added dropwise into cold acetone, the precipitate formed was collected by filtration, and 21 g of purified hydrogenated phospholipid (sample 2) was obtained. The phospholipid composition of the samples thus obtained is given in Table 1. Sample 2 did not contain any glycolipid.

TABLE 1

| Sample | Neutral Fat | PE | PC | LPC | Glycolipid |
|---|---|---|---|---|---|
| No. 1 | 3.9% | 7.0% | 77.5% | 3.0% | 8.7% |
| No. 2 | 0 | 3.0 | 95.0 | 2.0 | 0 |

PE = phosphatidylethanolamine
PC = phosphatidylcholine
LPC = lysophosphatidylcholine Method for analysis of phospholipid composition in this invention is as follows:

The sample is spotted on a thin-layer, silica gel plate (Merck); the plate is developed with chloroform-methanol-water (65:25:4, v/v). After removal of the solvent, the plate is sprayed with a sulfuric acid solution of 2% cerium (IV) sulfate and then heated at 110° C. for 20-30 minutes, which caused the spots for phospholipid and glycolipid to become black, forming the chromatogram shown in FIG. 1. This chromatogram was scanned with a Shimadzu Model CS-910 chromatoscanner for quantitative determination of each spot. The area of each spot was expressed as a percentage of the whole to calculate the composition of phospholipid.

The glycolipid content in this invention refers to the sum of GL(II)+GL(III)+GL(IV)+GL(V) in FIG. 1, and is determined by the method outlined above.

In FIG. 1, the symbols have the following meaning:
FL(I) to GL(V): glycolipid
PL: unidentified phospholipid
LPC: lysophosphatidylcholine
X: unidentified substance
Y: unidentified substance
TG: neutral lipid
PS: phosphatidylserine
PC: phosphatidylcholine
PE: phosphatidylethanolamine

EXAMPLE 3

In a 6-liter autoclave 900 g of soybean phospholipid (sample 1) was extracted with ethanol in the same manner as in Example 2, 3 liters of ethanol and 5% Raney nickel were added, and hydrogenation was carried out with a hydrogen pressure of 15.3 kg/cm² for 18 minutes. After evaporation of the solvent, 500 g of the residue (sample 2) was dissolved in chloroform-methanol mixture (1:1, v/v), 2.5 kg of activated alumina was added, and the mixture was stirred at room temperature for one hour. The chloroform-methanol layer was decanted, the catalyst was removed by centrifugation and filtration through a paper filter and the solution was filtered through a Millipore ® filter. Evaporation of the solvent from the filtrate gave purified soybean phospholipid (sample 3) with an iodine value of 41.6. The phospholipid compositions of samples 1, 2 and 3 are given in Table 2. The glycolipid content of sample 3 was 2.7%.

Symbols used in Table 2 have the same meaning as stated above.

TABLE 2

| Sample No. | TG | Y | X | PL | PE | PC | PS | LPC | GL |
|---|---|---|---|---|---|---|---|---|---|
| 1 | 3.1% | 2.7% | 3.5% | 4.3% | 18.7% | 45.3% | 0.5% | 0.7% | 17.6% |
| 2 | 11.0 | 0 | 2.4 | 2.5 | 9.4 | 59.1 | 0 | 0.9 | 11.6 |
| 3 | 3.6 | 1.6 | 0 | 2.3 | 0.3 | 87.9 | 0 | 1.9 | 2.7 |

EXAMPLE 4

To a solution of 1 kg of soybean phospholipid, extracted with ethanol in the same manner as in Example 2, and dissolved in 3 liters of ethanol, 5% Raney nickel was added and hydrogenation was carried out at a hydrogen pressure of 17.4 kg/cm² for 35 minutes. After evaporation of the solvent, five 8 g samples of the residue (sample 1) with an iodine value of 39.5 were each dissolved in 150 ml of a chloroform-methanol mixture (1:1, v/v), and 8, 16, 24, 32 and 40 g respectively of activated alumina were added to these solutions. The mixtures were stirred at room temperature for one hour, alumina was filtered off, and the filtrate was passed through a Millipore ® filter. The filtrate was evaporated to dryness to obtain samples Nos. 2, 3, 4, 5, and 6, their yields being 3.0, 3.0, 5.5, 6.5 and 7.7 g respectively. The glycolipid contents of these samples are given in Table 3.

TABLE 3

| Sample No. | Alumina used (g) | Glycolipid content (%) |
|---|---|---|
| 1 | — | 19.6% |
| 2 | 8 | 20.9 |
| 3 | 16 | 18.9 |
| 4 | 24 | 16.8 |
| 5 | 32 | 14.3 |
| 6 | 40 | 3.5 |

EXAMPLE 5

A mixture of 3 kg of soybean lecithin for foodstuff and 11 liters of 95% ethanol was stirred for one hour, the ethanol layer was collected, and 5 volumes of acetone was added to it, producing 1 kg of a precipitate which was taken as the ethanol-extracted soybean phospholipid. To this precipitate, 3 liters of ethanol and 5% of a catalyst were added, and the mixture was hydrogenated at a hydrogen pressure of 50 kg/cm² for 30 minutes. This resulted in a hydrogenated soybean phospholipid with an iodine value of 40.

To a solution of 5 g of hydrogenated soybean phospholipid so obtained and dissolved in 50 ml of a solvent with warming, 25 g of activated alumina was added and the mixture was stirred for one hour. Alumina was filtered off, the filtrate was passed through a Millipore ® filter, and the filtrate was evaporated to dryness under reduced pressure. The solvent used was ethanol containing 5% hexane, ethanol containing 5% water, 99.5% ethanol, ethanol containing 5% methanol, or a mixture of dichloroethylene and ethanol containing 5% water (1:1, v/v).

Compositions of the purified phospholipids so obtained are given in Table 4.

TABLE 4

| Sample No. | Solvent No.* | TG | Y | X | PL | PE | PC | LPC | GL |
|---|---|---|---|---|---|---|---|---|---|
| 1 | 1 | 1.0% | 3.6% | 0% | 2.3% | 0% | 91.8% | 1.1% | 0.2% |
| 2 | 2 | 1.5 | 4.3 | 0 | 3.0 | 0 | 88.1 | 2.1 | 0.8 |
| 3 | 3 | 1.3 | 4.1 | 0 | 2.8 | 0 | 90.7 | 1.2 | 0 |
| 4 | 4 | 1.2 | 3.9 | 0 | 2.3 | 0 | 91.0 | 1.5 | 0 |
| 5 | 5 | 1.1 | 3.6 | 0 | 5.0 | 0 | 85.2 | 1.0 | 4.1 |

*Solvent
1 Ethanol containing 5% hexane
2 Ethanol containing 5% water
3 99% ethanol
4 Ethanol containing 5% methanol
5 Dichloroethylene-ethanol containing 5% water (1:1, v/v).

The symbols have the same significance as those used in Table 2.

EXAMPLE 6

Five kinds of purified hydrogenated soybean phospholipid with iodine values of 19.7, 25.4, 36.3, 49 and 71 were used. Mixtures consisting of 24 g of each one of these phospholipids, 200 g of purified soybean oil, 50 g of glycerol JP, and 1,726 g of distilled water for injection were emulsified in a high-pressure emulsifying machine (product of Manton-Gaulin) in a nitrogen stream at a pressure of 650 kg/cm$^2$. The five fat emulsions thus obtained were filtered through a Millipore ® filter (1.2 μm pores), and the filtrate was sterilized by heating at 120° C. for 20 minutes at one atmosphere for use in the following animal experiment.

Male Sprague-Dawley (SD) strain rats, weighing 150 g, were given injections in the tail vein of 60 ml/kg body weight of one of the fat emulsions for 10 days continuously, with all five emulsions obtained being used.

The rate of injection was 3-5 ml/min. After consecutive injection for 10 days, the rats were fasted overnight, blood was collected by the conventional method, and the hematocrit value and neutral fat and phospholipid in the plasma were determined.

In order to examine accumulative residue of neutral lipid in the spleen, rats were given one 60 ml/kg injection of one or the other of the emulsions, and fasted overnight. Their spleens were excised to measure neutral fat in the organ by the conventional method.

Figure 2:
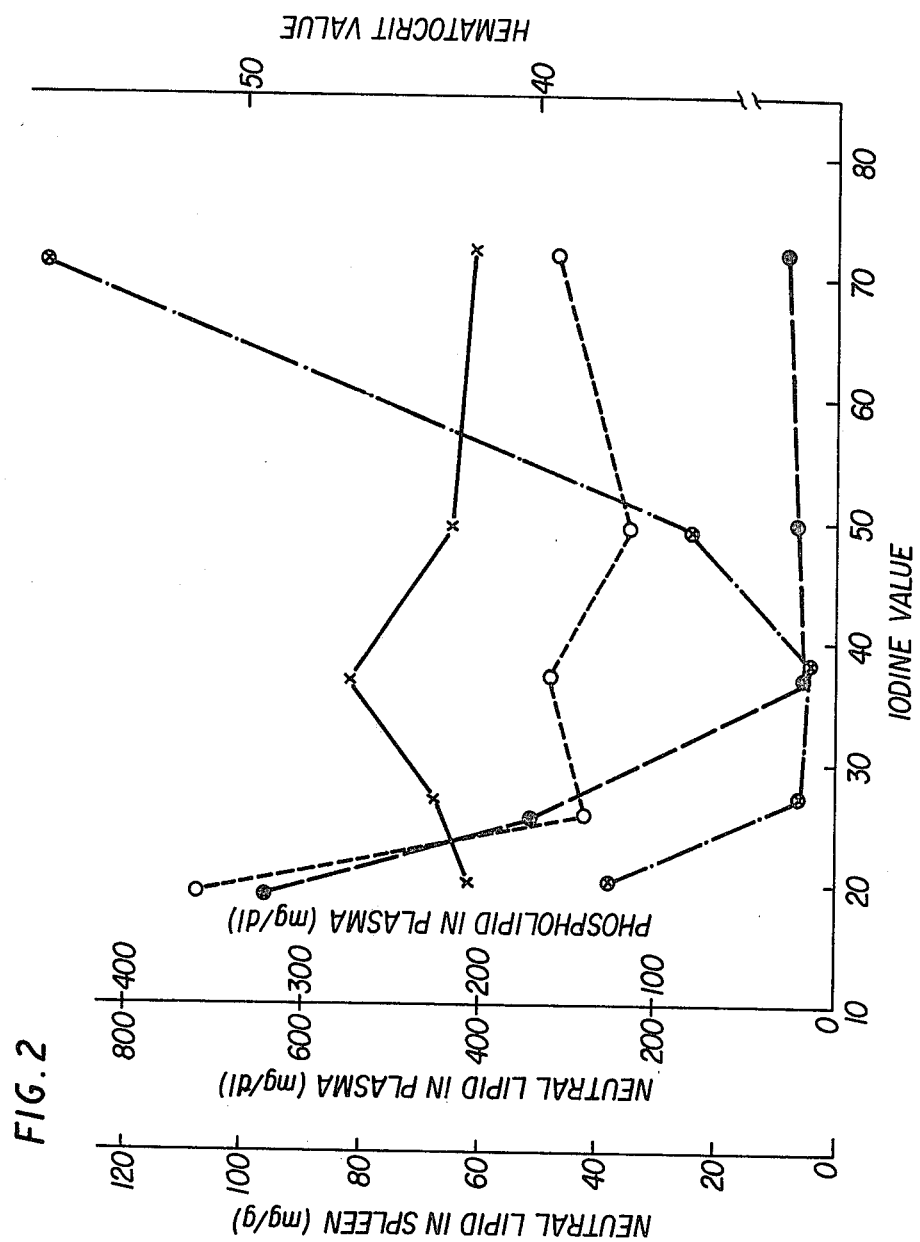
FIG. 2 is a plot illustrating the results obtained in the experiments of Example 6.

The results of this animal experiment are shown in FIG. 2. The high hematocrit value and low neutral lipid and phospholipid in the spleen were found in those animals injected with a fat emulsion using hydrogenated phospholipids with iodine values of 30-50.

In FIG. 2 ☒ represents neutral lipid in the spleen, X the hematocrit, o phospholipid in the plasma, and the neutral lipid in the plasma.

EXAMPLE 7

Sample Nos. 1 and 2 obtained in Example 2 were emulsified in a highpressure emulsification machine by the same method as in Example 6, sterilized by heat, and fat emulsions for intravenous injection were prepared. Emulsification was carried out under a pressure of 600 kg/cm$^2$ and repeated six times.

The fat emulsions thus obtained were injected into the tail vein of SD strain male rats, weighing ca. 200 g (test groups of three rats each), at a dose of 60 ml/kg body weight. Test group 1 received an emulsion prepared using the emulsifier of sample no. 1 of Example 2, test group 2 received emulsion prepared using the emulsifier of sample no. 2 of Example 2 (emulsion according to the invention). The rats were fasted overnight and the spleens collected to examine the accumulation of neutral fat. The control rats were injected with either a fat emulsion made with commercial egg yolk phospholipid (test group 3) or physiological saline solution (test group 4). Comparative results are shown in Table 5.

TABLE 5

| Test Group | Residual amount of neutral fat in the spleen (mg/g) |
|---|---|
| 1 | 12.05 ± 2.89 |
| 2 | 2.10 ± 0.12 |
| 3 | 14.26 ± 8.07 |
| 4 | 2.16 ± 0.27 |

The fat emulsion according to the invention prepared using the emulsifier of sample no. 2 of Example 2 was also administered to the tail veins of SD strain male rats, weighing ca. 150 g (test groups of three each), in a dose of 100 ml/kg body weight, for 10 consecutive days (test group 1). The rats were then fasted overnight, the blood, spleen and liver were collected, and the hemotocrit value, erythrocyte counts, neutral fat, and phospholipid were measured. Fat emulsion prepared with commercial egg yolk phospholipid was administered as one control (test group 2); another group (test group 3) received no fat emulsion. These results are given in Table 6.

It will be seen from Tables 5 and 6 that fat emulsion using soybean phospholipid from which glycolipid was removed after hydrogenation is desirable as a fat emulsion for intravenous injection.

TABLE 6

| Test Group | Hematocrit (%) | Erythrocyte counts (10$^4$/mm$^3$) | Lipid in plasma (mg/dl) | | Neutral fat in organs (mg/g) | |
|---|---|---|---|---|---|---|
| | | | Neutral fat | Phospholipid | Spleen | Liver |
| 1 | 44.0 ± 1.1 | 665 ± 8 | 69 ± 14 | 299 ± 27 | 2.99 ± 0.28 | 9.62 ± 1.01 |
| 2 | 43.3 ± 1.1 | 642 ± 62 | 62 ± 7 | 346 ± 101 | 4.63 ± 0.62 | 25.3 ± 11.8 |
| 3 | 46.3 ± 1.1 | 664 ± 28 | 40 ± 6 | 129 ± 9 | 2.81 ± 0.32 | 14.9 ± 3.6 |

EXAMPLE 8

Fat emulsions were prepared by using the phospholipid of sample 3 obtained in Example 3 and emulsified by the method of Example 6. These fat emulsions were injected into the tail veins of SD strain male rats, weighing 140 g (test groups of four each), in a dose of 100 ml/kg body weight for 10 consecutive days (test group 1). The rate of injection was 3-5 ml/min. Various tests were then made and compared with control rats given an emulsion made with commercial egg yolk lecithin (test group 2) or physiological saline solution (test group 3), and untreated controls (test group 4). Results are given in Table 7.

From the results it is evident that the phospholipid obtained in this invention does not cause anemia, while residual neutral lipid and phospholipid in blood is low. Accordingly, it exhibits desirable properties as an emulsifier for intravenously administered fat emulsions.

TABLE 7

| Test Group | Hematocrit (%) | Erythrocyte counts ($10^4/mm^3$) | Lipid in plasma (mg/dl) | |
|---|---|---|---|---|
| | | | Neutral lipid | Phospholipid |
| 1 | 43.8 ± 1.3 | 640 ± 15 | 56 ± 10 | 134 ± 19 |
| 2 | 43.1 ± 0.8 | 669 ± 12 | 105 ± 11 | 294 ± 68 |
| 3 | 45.3 ± 0.9 | 633 ± 27 | 68 ± 10 | 109 ± 12 |
| 4 | 45.0 ± 1.2 | 641 ± 5 | 62 ± 4 | 105 ± 7 |

EXAMPLE 9

Fat emulsions were obtained by using phospholipid (samples 2-6) obtained in Example 4 and emulsified by ultrasonication. Emulsification conditions were 25 KHz for two hours. The fat emulsions so obtained were injected into the tail veins of SD strain male rats, weighing ca. 200 g (test groups of three each), in a single dose of 60 ml/kg body weight, and accumulative residue of neutral fat in the spleen was examined. The results, shown in Table 8, indicates that the accumulation of neutral fat in the spleen is lower the less the amount of glycolipid.

TABLE 8

| Test Group | Emulsifier of Example 4 | Residual amount of neutral lipid in spleen (mg/g) |
|---|---|---|
| 1 | Sample 2 | 169.2 ± 15.5 |
| 2 | Sample 3 | 55.7 ± 25.4 |
| 3 | Sample 4 | 29.9 ± 7.1 |
| 4 | Sample 5 | 21.9 ± 13.0 |
| 5 | Sample 6 | 20.9 ± 7.8 |

EXAMPLE 10

Fat emulsion was obtained by using sample 1 obtained in Example 5 and by the same method as that of Example 6, and was administered to rats (test groups of four each) in the same manner as in Example 8 (test group 1). The rats weighed ca. 100 g. Controls received either fat emulsions prepared using commercial egg yolk phospholipid (test group 2) or physiological saline (test group 3). Results are given in Table 9.

TABLE 9

| Test Group | Hematocrit (%) | Erythrocyte counts ($10^4/mm^3$) | Lipid in plasma (mg/dl) | |
|---|---|---|---|---|
| | | | Neutral lipid | Phospholipid |
| 1 | 41.8 ± 1.1 | 614 ± 34 | 45 ± 6 | 169 ± 16 |
| 2 | 41.3 ± 1.3 | 612 ± 41 | 71 ± 10 | 274 ± 72 |
| 3 | 45.1 ± 1.6 | 630 ± 19 | 44 ± 12 | 108 ± 13 |

EXAMPLE 11

The fat emulsion used for test group 1 in Example 8 was used to test acute toxicity in SD strain male rats, weighing ca. 200 g. The $LD_{50}$ value obtained was 142 ml/kg body weight. Subacute toxicity test was carried out by 30 continuous administrations of 20 or 40 ml/kg body weight, but none of the rats died. Their body weight increased at the same rate as that of rats give physiological saline solution, and there was no evidence of anemia. The fat emulsion obtained by this invention was thus found to be fully safe.

EXAMPLE 12

Figure 3:
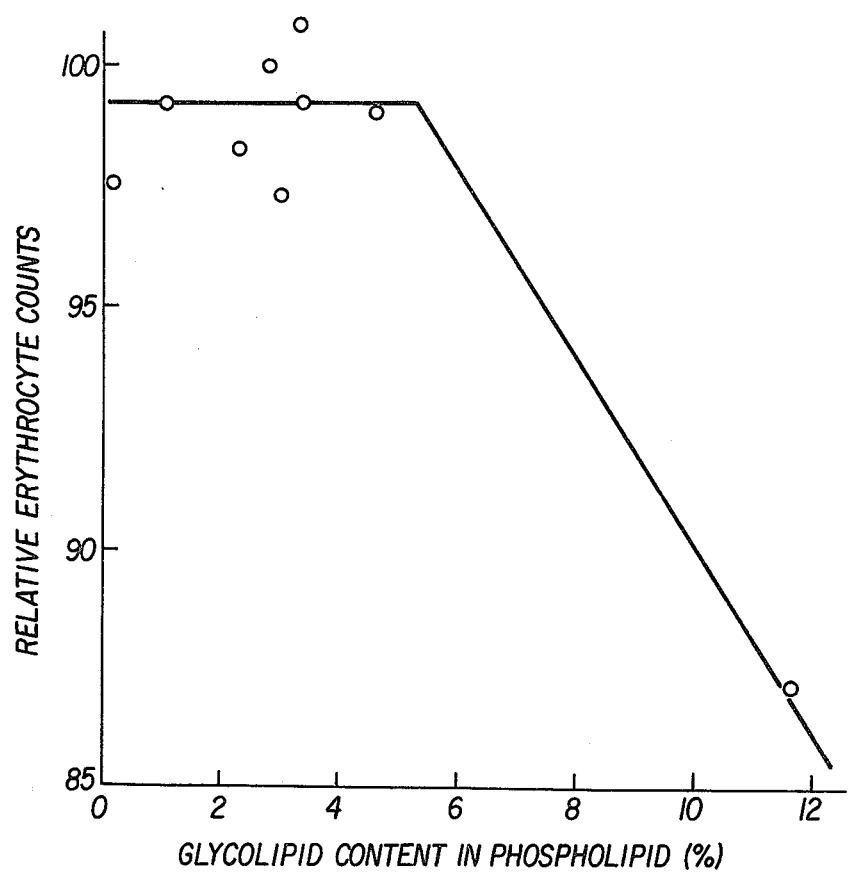
FIG. 3 is a plot showing the results obtained in the experiments of Example 12.

Purified soybean phospholipid with glycolipid content of 0-11.6% was obtained by the same methods as described in Examples 2, 3 and 4. These were used as emulsifiers, and emulsification was carried out by the same method as described in Example 7 to obtain fat emulsions for intravenous injection. These emulsions were injected into the tail veins of SD strain male rats, in a dose of 100 ml/kg body weight, continuously for 10 days. The rats were fasted overnight after completion of the injections, blood was collected from the inferior vena cava, and the erythrocyte counts were measured. The control rats were injected with physiological saline solution. The erythrocyte counts in the control blood were taken as 100, and the erythrocyte counts in rats injected fat emulsions were expressed by a relative value. Relationship between the glycolipid content and relative number of erythrocyte counts is given in FIG. 3. It is clear from FIG. 3 that anemia is not produced with a glycolipid content of less than 5%.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. An emulsifier comprising purified phospholipid of soybean origin, containing less than 5% of glycolipid by weight, and having a degree of hydrogenation of 30-50 as defined by the iodine number.

2. The emulsifier of claim 1, having a degree of hydrogenation of 35-45 as defined by the iodine value.

3. The emulsifier of claim 1 prepared by a process comprising:
   (1) isolating a phosphatidylcholine fraction from said phospholipid of soybean origin;
   (2) partially hydrogenating said isolated phosphatidylcholine fraction; and
   (3) removing glycolipid from said hydrogenated phosphatidylcholine fraction.

4. The emulsifier of claim 3, wherein the degree of hydrogenation of said partially hydrogenated phosphatidylcholine fraction is 30-50 as defined by the iodine value.

5. The emulsifier of claim 3, wherein the degree of hydrogenation of said partially hydrogenated phosphatidylcholine fraction is 35-45 as defined by the iodine value.

6. The emulsifier of claim 3, which has been sterilized by aseptic filtration.

7. A fat emulsion for intravenous injection comprising a fatty oil, water and the emulsifier of claim 1.

8. A fat emulsion for intravenous injection comprising a fatty oil, water and the emulsifier of claim 3.

9. The fat emulsion of claim 7 or 8, wherein the ratio of fatty oil to water is between about 4:1 and about 20:1 by weight.

10. The fat emulsion of claim 7 or 8, wherein the amount of said emulsifier is from 0.5 to 5 parts by weight per 10 parts of fatty oil.

11. The fat emulsion of claim 7 or 8, wherein the amount of said emulsifier is from about 0.5 parts by weight to about 3 parts per 10 parts of fatty oil.

12. The fat emulsion of claim 7 or 8, wherein the amount of said emulsifier is from about 0.75 parts by weight to about 1.5 parts per 10 parts of fatty oil.

13. The fat emulsion of claim 7 or 8, wherein said fatty oil is a pharmaceutically acceptable fatty oil.

14. The fat emulsion of claim 7 or 8, wherein said fatty oil is purified soybean oil.

15. A process for preparing a purified emulsifier of soybean origin from a soybean phospholipid comprising:
  (1) isolating a fraction containing phosphatidylcholine from said soybean phospholipid;
  (2) partially hydrogenating said soybean phospholipid; and
  (3) removing glycolipid from said soybean phospholipid wherein, steps (1), (2) and (3) may be performed in any order.

16. The process of claim 15 further comprising sterilizing said purified emulsifier by aseptic filtration.

17. The process of claim 15, wherein said partial hydrogenation is conducted so as to produce a degree of hydrogenation of 30–50 as defined by the iodine value of said partially hydrogenated phosphatidylcholine fraction.

18. The process of claim 15, wherein said partial hydrogenation is conducted so as to produce a degree of hydrogenation of 35–45 as defined by the iodine value of said partially hydrogenated phosphatidylcholine fraction.

19. A process according to claim 15, wherein step 1) is performed first.

20. A process for preparing a purified emulsifier of soybean origin comprising:
  (1) isolating a phosphatidylcholine fraction from a phospholipid of soybean origin;
  (2) partially hydrogenating said isolated phosphatidylcholine fraction; and
  (3) removing glycolipid from said hydrogenated phosphatidylcholine fraction.

* * * * *